United States Patent [19]

Mader

[11] Patent Number: 4,885,416
[45] Date of Patent: Dec. 5, 1989

[54] FLUORINATION PROCESS

[75] Inventor: Frederick W. Mader, Kennett Square, Pa.

[73] Assignee: E. I. Du Pont De Nemours and Company, Wilmington, Del.

[21] Appl. No.: 154,421

[22] Filed: Feb. 9, 1988

Related U.S. Application Data

[63] Continuation of Ser. No. 789,288, Oct. 18, 1985, abandoned, which is a continuation-in-part of Ser. No. 507,084, Jun. 23, 1983, abandoned.

[51] Int. Cl.$^4$ .................. C07C 17/20; C07C 17/22; C07C 19/02; C07C 19/08
[52] U.S. Cl. .................................... 570/170; 570/167
[58] Field of Search ........................... 570/170, 167

[56] References Cited

U.S. PATENT DOCUMENTS

| | | | |
|---|---|---|---|
| 1,978,840 | 10/1934 | Henne | 570/170 |
| 2,005,705 | 6/1935 | Daudt et al. | 570/170 |
| 2,005,708 | 6/1935 | Daudt et al. | 570/170 |
| 2,005,711 | 6/1935 | Daudt et al. | 570/170 |
| 2,510,872 | 8/1984 | Downing | 570/170 |
| 2,786,738 | 3/1957 | Ruh et al. | 570/167 |
| 3,240,826 | 3/1966 | Davis | 570/170 |
| 4,078,007 | 3/1978 | Ferstandig | 570/170 |
| 4,091,043 | 5/1978 | Ohsaka et al. | 570/170 |
| 4,438,088 | 3/1984 | Weaver | 570/170 |

FOREIGN PATENT DOCUMENTS

| | | | |
|---|---|---|---|
| 589167 | 6/1947 | United Kingdom | 570/170 |
| 925909 | 5/1963 | United Kingdom | 570/167 |

OTHER PUBLICATIONS

Advances In Fluorine Chemistry, Stacey et al, vol. 3, pp. 117 and 146–154, Butterworths & Co. Ltd., London (1963).

Primary Examiner—J. E. Evans
Attorney, Agent, or Firm—Charles E. Feeny

[57] ABSTRACT

A continuous process for florinating haloalkanes containing at least one nonfluorine halogen atom wherein antimony pentachloride is reacted with HF to produce an antimony (V) chlorofluoride and HCl is removed. The antimony chlorofluoride thus produced is then transferred to a separate reaction zone where it is reacted with the haloalkane, thereby replacing a portion of the nonfluorine halogen in the haloalkane with fluorine of the antimony (V) chlorofluoride.

28 Claims, 5 Drawing Sheets

FLUORINATION PROCESS

CROSS-REFERENCE TO RELATED APPLICATION

This application is a continuation of application Ser. No. 789,288 filed Oct. 18, 1985, now abandoned, which in turn is a continuation-in-part of application Ser. No. 507,084 filed June 23, 1983, now abandoned.

FIELD OF INVENTION

This invention relates to a continuous process for manufacturing fluorinated derivatives of alkanes.

BACKGROUND OF THE INVENTION

Fluorination of a haloalkane by exchange of fluorine for another halogen is the most generally used technique for preparing fluorinated alkanes. It is not usually practical to react a mixture of a haloalkane with HF as the reaction proceeds sluggishly and requires very high temperatures and pressures. In 1892 Swartz synthesized $CCl_3F$ in a liquid phase reaction in which the reaction product of $SbF_3$ and $Br_2$ was contacted with $CCl_4$; Bull. Acad. R. Belg., 1892(3), 24, 309. However, it was not until 1926 that $CF_4$, the simplest perfluorocarbon, was isolated. At just about that point, the needs of the refrigeration industry prompted considerable development in the field. The first commercial synthesis developed thereafter (about 1930) was a continuous process wherein hydrogen fluoride and haloalkanes containing halogen other than fluorine were reacted in the presence of antimony pentachloride; Daudt et al., U.S. Pat. Nos. 2,005,705 and 2,005,708. The reaction is that of replacing Cl, Br or I of the haloalkane with fluorine of the hydrogen fluoride. Most generally, the haloalkanes of choice are chloroalkanes because of their availability and their tendency to undergo fewer side reactions during the exchange reaction than their bromo or iodo analogs. The fluorination reaction may be represented by the following equation using chloroform as the illustrative haloalkane:

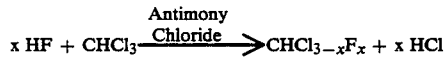

wherein x is 1–3. The process is carried out by continuously cofeeding hydrogen fluoride and haloalkane into antimony pentachloride. Generally, a mixture of $CHCl_2F$, $CHClF_2$ and $CHF_3$ is obtained, the particular proportion of the fluorinated products depending upon the reactant ratios and the reaction conditions. For each mol of hydrogen fluoride undergoing the exchange reaction, one mol equivalent of hydrogen chloride is generated. Usually HF is used in excess so as to ensure maximum utilization of the haloalkane reactant. Therefore, the crude reaction product will contain HF as well as a mixture of $CHCl_2F$, $CHClF_2$, $CHF_3$ and HCl.

Despite a number of disadvantages in it, the above-described continuous process has been the primary manufacturing process for preparing virtually all of the major fluorocarbons and chlorofluorocarbons which have been manufactured since industrial production of them commenced. Since the beginning of industrial production of such products, efficient utilization of HF, its removal from products and by-products of the reaction, and its recovery for re-use have been important considerations. In addition, it is necessary to remove virtually all by-product HCl in addition to significant amounts of HF which are found in the crude reaction product as an azeotrope with the fluorinated reaction products. Another factor which complicates purification of the fluorinated reaction products resides in the fact that boiling points of some of the fluorinated products overlap the boiling point of HCl or are not far removed from the boiling point of HF. For example, in the fluorination of chloroform, the crude reaction product includes $CHCl_2F$ (b.p. 8.9° C.), $CHClF_2$ (b.p. $-40.8°$ C.), $CHF_3$ (b.p. $-82°$ C.), HCl (b.p. $-85°$ C.) and HF (b.p. 19.4° C.). Moreover, the production of $CHF_3$ normally exceeds its demand, so that its overproduction constitutes an economic penalty.

Aqueous scrubbing of the reaction product can be used to remove the by-product HCl and unreacted HF; Daudt et al. U.S. Pat. No. 2,005,705. However, such an approach is an uneconomic one since it sacrifices most of the HF as waste and necessitates subsequent sale of the by-product HCl as a 30% aqueous solution; Hamilton, Advances in Fluorine Chemistry, Vol. 3, Butterworth (1963). Separation of products from by-products and unreacted HF has been accomplished by use of series of distillation techniques. But that means of purifying the products requires a great deal of energy for refrigeration and the installation of a great deal of pressurized equipment, resulting in high capital costs for construction of manufacturing facilities and high operating costs as well. Moreover, such anhydrous pressured distillation techniques do not effect separation of fluorinated product/HF azeotropes. Further processing is required, such as scrubbing with water (U.S. Pat. No. 2,450,414) or concentrated $H_2SO_4$ (U.S. Pat. No. 3,873,629).

The corrosivity of HF is well known. In the presence of small amounts of antimony pentachloride (used in the continuous process described above), its corrosivity increases dramatically. The reactor systems used in the prior art continuous process have been known to fail because of corrosion. That effect is attributable to the fact that in that process, HF and the chlorocarbon are continuously fed into a static charge of antimony pentachloride, a liquid under the reaction conditions, in a reactor system that contains no mechanical agitation. As a consequence, there is a very high mol ratio of HF to antimony pentachloride at the point at which the HF first comes in contact with the antimony pentachloride. At such a high HF to antimony pentachloride ratio, the corrosivity of the mixture increases dramatically.

It is therefore an object of the present invention to provide an economical, energy-efficient, continuous process for the production of fluorinated haloalkanes. It is a further object of the present invention to provide a continuous haloalkane fluorination process which will provide crude fluorinated products substantially free of hydrogen halides, in particular $CHClF_2$ free of its azeotrope with HF, and $CHF_3$ as well as $CClF_3$ free of close-boiling HCl. It is a still further object of the present invention to provide a continuous haloalkane fluorination process which minimizes costs associated with the purification of reaction products. It is another object of the present invention to provide a continuous haloalkane fluorination process which results in reduced corrosion of equipment used in the process. It is still another object of the present invention to provide a continuous haloalkane fluorination process which results in waste streams that are environmentally more acceptable. Yet another object of the present invention is to provide a continuous haloalkane fluorination process in which anhydrous HCl is recovered substantially free of HF and fluorinated haloalkanes. Still another object of the present invention is to provide greater flexibility in the production of fluorinated chloromethanes in which the overproduction of low-demand fluorinated products, such as $CHF_3$, can be controlled and minimized as desired. A still further object of the present invention is to provide a continuous haloalkane fluorination process in which the utilization of HF is essentially complete. These and other objects will be apparent from the description provided herein.

BRIEF SUMMARY OF THE INVENTION

The present invention relates to a continuous process for fluorinating haloalkanes in which one continuously fluorinates antimony pentachloride to an antimony (V) chlorofluoride by continuously supplying said antimony pentachloride and hydrogen fluoride to a reaction zone while continuously removing by-product hydrogen chloride gas from the antimony (V) chlorofluoride thus produced. Thereafter said antimony chlorofluoride is fed continuously to a separate reaction zone to which is also supplied continuously a fluorinatable haloalkane containing at least one nonfluorine halogen atom, and reacting said antimony chlorofluoride with said haloalkane so as to replace a portion of the nonfluorine halogen in said haloalkane with fluorine from said antimony chlorofluoride, and continuously recovering the fluorinated reaction product or products thereby produced.

DETAILED DESCRIPTION OF THE INVENTION

One embodiment of the invention involves (1) continuously contacting antimony pentachloride with hydrogen fluoride in a first zone to replace a portion of chlorine in said antimony pentachloride with fluorine, (2) transferring the thus fluorinated antimony pentachloride to a second zone wherein the fluorination of antimony pentachloride to antimony (V) chlorofluoride is substantially completed and hydrogen chloride generated in said fluorination of antimony pentachloride is separated from said antimony chlorofluoride, (3) transferring said antimony chlorofluoride to a third zone wherein it is contacted with a fluorinatable haloalkane containing at least one halogen other than fluorine to replace at least a portion of the nonfluorine halogen atoms of said haloalkane with fluorine, (4) removing spent antimony (V) chlorofluoride from said third zone into a fourth zone wherein said spent antimony chlorofluoride is freed of volatile material and then recycled to the first zone for refluorination with hydrogen fluoride, and (5) removing fluorinated haloalkanes from said third zone to a separation means to recover fluorinated haloalkanes essentially free of hydrogen halide.

Figure 1:
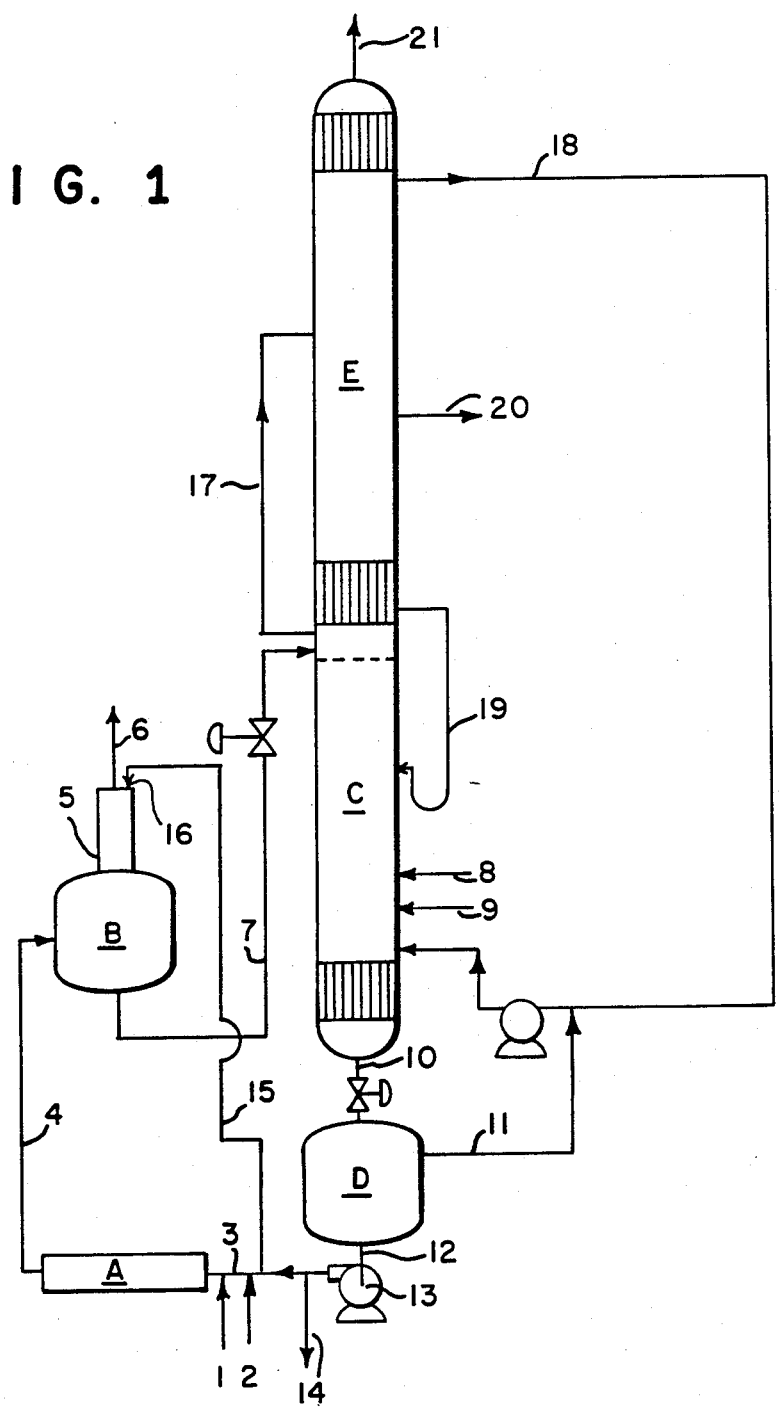
FIG. 1 depicts an embodiment of the present invention.

The foregoing embodiment of the invention, using chloroform as the haloalkane, can be illustrated by reference to FIG. 1. Antimony pentachloride is introduced into first zone A via lines 1 and 3 while hydrogen fluoride is introduced into zone A via lines 2 and 3. The hydrogen fluoride reacts with the antimony pentachloride in zone A replacing a portion of the chlorine atoms with fluorine. The reaction in this first zone can be carried out at temperatures ranging from about 30° C. to about 140° C. A preferred temperature range is from about 70° C. to about 120° C., while a temperature between about 90° C. and 100° C. is most preferred.

The chemical reaction taking place in zone A may be represented by the following equation:

$$SbCl_5 + xHF \rightarrow SbCl_{5-x}F_x + xHCl$$

The reaction mixture from zone A is transferred via line 4 to the second zone B which is a degassing vessel maintained at substantially the same temperature as the first zone. The reaction of hydrogen fluoride with antimony pentachloride proceeds to substantial completion in zone B if it is not already completed in zone A. Hydrogen chloride formed in the fluorination of the antimony pentachloride is removed from zone B via scrubber 5 and exit line 6. The introduction of antimony pentachloride via line 15 to scrubber 5 in a countercurrent fashion at juncture 16 assists in consuming any unreacted hydrogen fluoride that would otherwise be removed along with hydrogen chloride.

The antimony (V) chlorofluoride in zone B is transferred via line 7 to a third zone C, the haloalkane reactor, wherein it is contacted with chloroform introduced into C via line 8. The haloalkane reactor C is operated in the temperature range of from about 60° C. to 150° C., preferably from about 75° C. to about 125° C. Chlorine may also be introduced into C via line 9 to maintain the antimony in the pentavalent state. The major chemical reaction taking place in C may be represented by the following general equation:

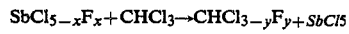

$$SbCl_{5-x}F_x + CHCl_3 \rightarrow CHCl_{3-y}F_y + SbCl_5$$

wherein $CHCl_{3-y}F_y$ represents a mixture of mono-, di- and trifluorinated products. It will be noted from the above reaction that there are no hydrogen halides to separate from the fluorinated products. It will be recognized, however, that small amounts of hydrogen halide will be present because of solubility of HCl in the antimony (V) chlorofluoride. The higher the pressure in Zone B the greater the solubility of HCl in the antimony (V) chlorofluoride, hence, the greater the amount of HCl that will be transferred from Zone B to Zone C along with the antimony (V) chlorofluoride and that will exit Zone C along with the organic products of the reaction. However, it will be appreciated that the amount of HCl thus transferred will be but a minor proportion of the stoichiometric amount produced in Zones A and B; i.e., the major proportion of the HCl will be vented via line 6 and recovered directly. Moreover, the antimony pentahalide remaining after the reaction with the haloalkane will usually contain a small proportion of residual fluoride, and will herein be referred to as spent antimony (V) chlorofluoride.

The spent antimony (V) chlorofluoride in zone C is passed via line 10 into a fourth zone D which is a degassing vessel wherein any unreacted haloalkane and fluorinated haloalkanes in the spent antimony (V) chlorofluoride are allowed to separate from the spent antimony (V) chlorofluoride and recycled to the haloalkane reactor C via line 11. Such separation may be facilitated by methods well-known in the art such as by reduction in pressure or by heating.

The spent antimony (V) chlorofluoride in zone D is then transferred via line 12 and pump 13 back to the first zone A. To alleviate contamination by impurities which build up in the system, a small portion of the spent antimony (V) chlorofluoride exiting from the pump 13 may be removed via line 14 and a corresponding amount of fresh antimony pentachloride may be introduced into the system via line 1.

The fluorinated products formed in the haloalkane reactor C which include dichloromonofluoromethane, monochlorodifluoromethane and trifluoromethane are transferred via line 17 distillation column E wherein the desired fluorinated products are separated. In contrast to prior art processes, the fluorinated products are substantially free of hydrogen halides, and therefore, the separation of the fluorinated products by distillation is easier and much less costly. The manner in which the distillation column is operated depends upon the particular component of the product mixture desired. For example, if chloroform is being fluorinated with the objective of producing monochlorodifluoromethane as the chief end product, it would be recovered via line 20 while trifluoromethane and dichloromonofluoromethane would be recycled to the haloalkane reactor C via lines 18 and 19, respectively, the former to be used to assist in stripping the fluorinated products from the spent antimony (V) chlorofluoride and the latter to be fluorinated. Higher boiling materials such as unreacted chloroform may also be recycled to C via line 19. When excessive amounts of trifluoromethane build up in the system, they may be recovered via line 21. The fluorinated haloalkanes produced by the process are useful as refrigerants, aerosol propellants, solvents and intermediates.

The hydrogen fluoride used to convert antimony pentachloride to antimony (V) chlorofluoride may be a pure product or a commercial grade of hydrogen fluoride which may contain small amounts of impurities. The presence of water in the reactants is not desirable, and therefore it is preferable to use substantially anhydrous hydrogen fluoride. The hydrogen fluoride may be either gaseous or liquid hydrogen fluoride.

The antimony chloride used is generally in the pentavalent form, but it may contain up to about 10% of the antimony in the trivalent form, preferably no more than about 4% for ease of handling. In order to maintain a desired high level of pentavalent antimony, chlorine gas may be introduced into the reactor to reoxidize any trivalent antimony formed by the action of reducing compounds present in the system.

The fluorination of antimony pentachloride with hydrogen fluoride may be carried out at atmospheric, subatmospheric or superatmospheric pressure. It is preferred to use superatmospheric pressures of up to about 20 atmospheres, particularly when liquified anhydrous HCl is to be recovered. The degree of fluorination of antimony pentachloride may be varied over a wide range such that fluorinated antimony (V) chlorofluorides contain from about 2% to about 23% by weight of fluorine, preferably from about 3% to about 14%. The antimony (V) chlorofluorides may be transferred to the degassing vessel B and subsequently to haloalkane reactor C using the pressure generated by the hydrogen chloride formed in the fluorination of the antimony pentachloride in vessel A, or by introduction of a pressurized inert gas such as nitrogen.

The degasser B is usually kept at a temperature approximating that of the antimony pentachloride fluorinator. In one embodiment, the pressure in the degasser B is less than the pressure in the antimony pentachloride fluorinator A in order to facilitate transfer of the fluorinated antimony (V) chloride from the fluorinator to the degasser using pressure differentials. On the other hand, the force needed to effect transfer may be mainly gravitational. The antimony (V) chlorofluoride is kept in the degasser for such time as is necessary to complete the reaction of hydrogen fluoride with antimony pentachloride and to separate substantially all of the by-product hydrogen chloride from the reaction mass. Usually the reaction of hydrogen fluoride and the desorption of by-product hydrogen chloride is rapid enough that a few minutes residence in the degasser is sufficient to accomplish these two objectives. Purging the antimony (V) chlorofluoride with an inert gas, such as nitrogen, can be used to ensure complete removal of HCl, particularly when superatmospheric pressure is used in vessel B.

The hydrogen chloride separated at the degasser may contain some residual hydrogen fluoride which can be converted to HCl by contacting the exiting hydrogen chloride stream with fresh antimony pentachloride or with spent antimony (V) chlorofluoride. The resulting hydrogen chloride can be collected as anhydrous hydrogen chloride or dissolved in water to form hydrochloric acid.

Contact between reactants in the haloalkane fluorination reactor C can be accomplished by conventional mixing methods such as by countercurrent or cocurrent flow, back mixing, etc. The pressure may be atmospheric, subatmospheric or superatmospheric, but generally it is preferred to use superatmospheric pressures of up to about 20 atmospheres, particularly when the haloalkane to be fluorinated is a one carbon atom haloalkane. An important consideration in the choice of pressure is that it is preferable to use a pressure that will maintain the antimony (V) halides in the liquid phase while allowing vaporization of fluorinated haloalkanes.

Figure 4:
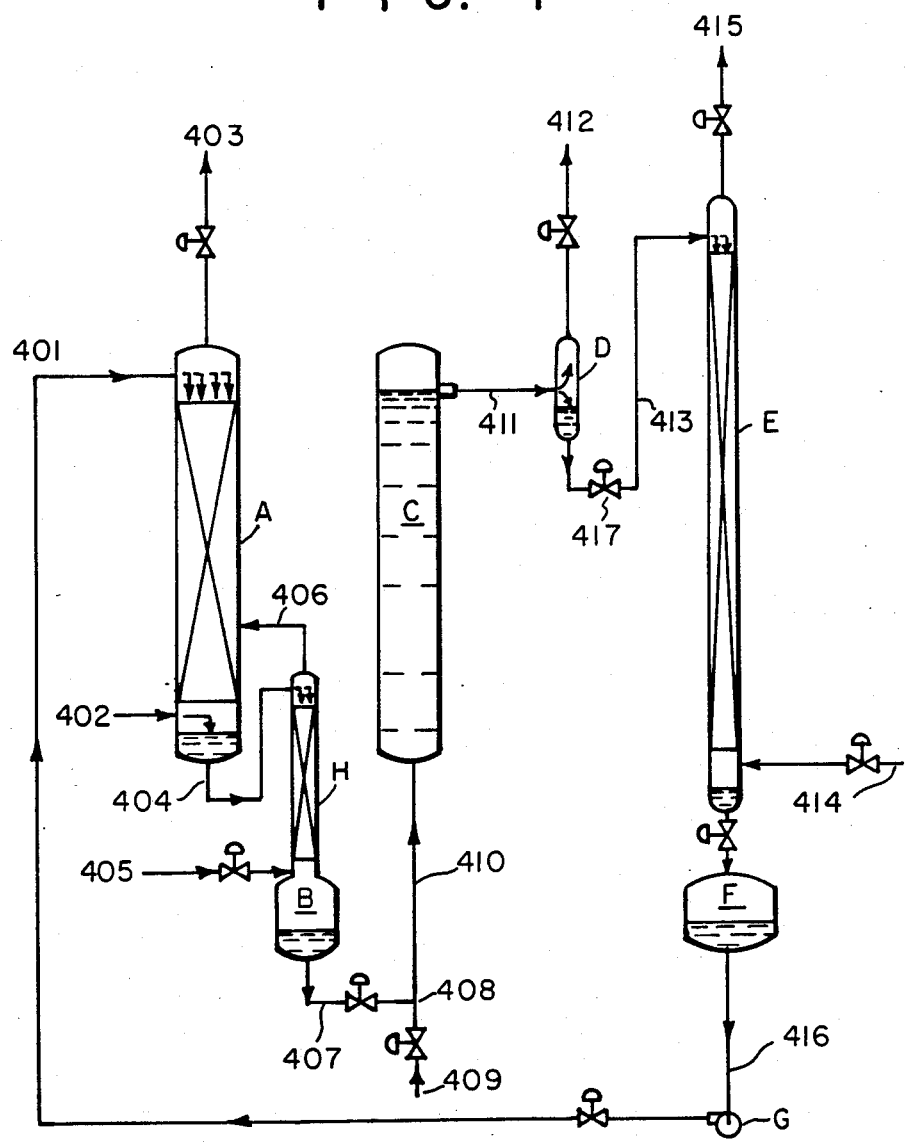
FIG. 4 shows a modification of the embodiment of FIG. 3 in which removal of by-product HCl is facilitated further.
Figure 5:
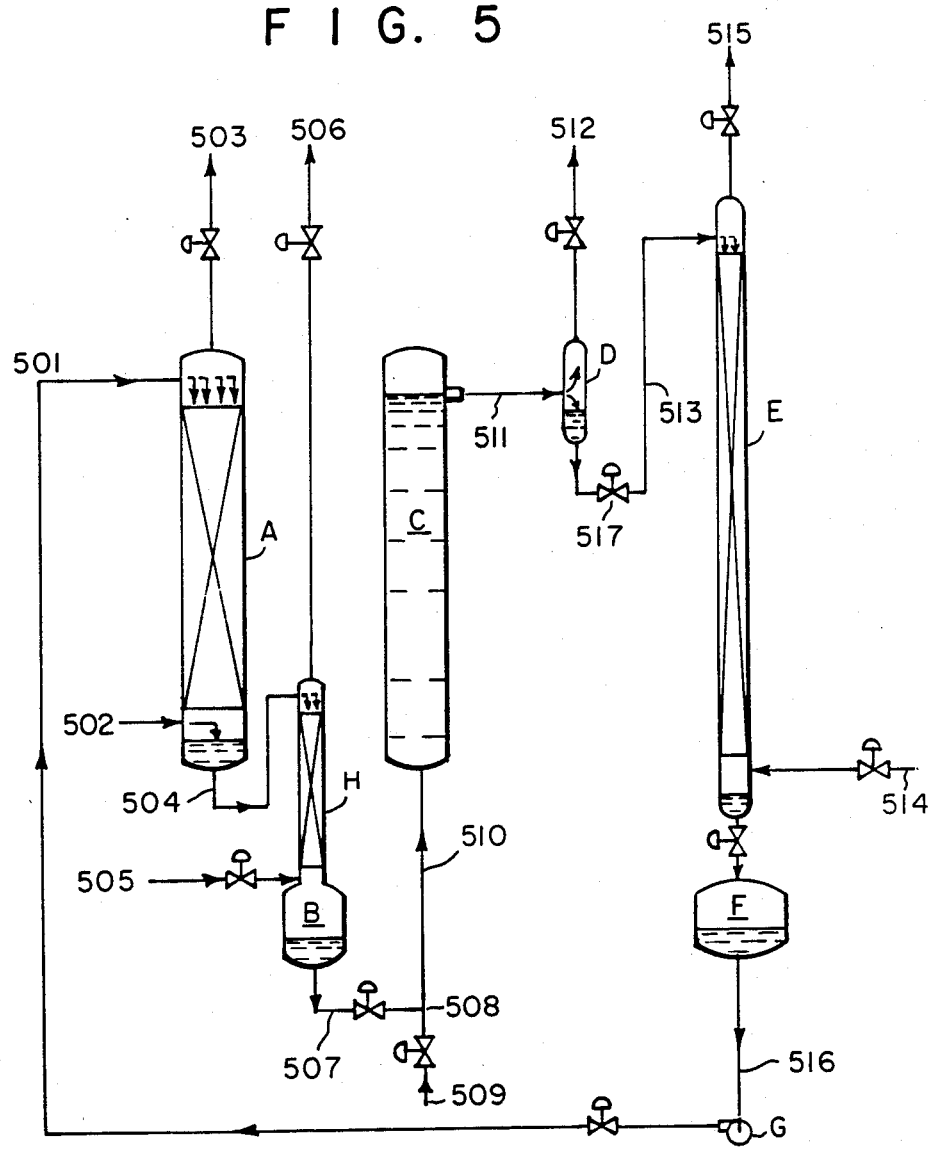
FIG. 5 is an alternative to the arrangement set forth in FIG. 4 for facilitating removal of by-product HCl.

In the preferred embodiment illustrated by FIG. 4, antimony pentachloride or spent antimony (V) chlorofluoride that has been used previously to fluorinate the haloalkane is fed continuously via line 401 to packed tower A, and hydrogen fluoride is fed continuously to packed tower A via line 402. The antimony (V) halide and the HF react with one another as they proceed through the tower countercurrently causing displacement of chlorine from the antimony (V) halide by fluorine from HF. The reaction results in evolution of HCl which is removed from tower A via line 403. The antimony (V) chlorofluoride formed in the reaction is transferred via line 404 to the top of a packed column H. Nitrogen is introduced at the base of packed column H via line 405, thereby stripping out HCl dissolved in the antimony (V) chlorofluoride, and transmitting it via line 406 back into packed tower A.

As indicated above, the reaction can be carried out at subatmospheric, atmospheric, or superatmospheric pressure and temperatures within the range between 30° and 140° C. In this embodiment of the invention, it is preferable to carry out the reaction in packed column A at a pressure between 250 and 350 psig, most preferably 300 psig. The temperature in the packed column should be sufficient so as to ensure that the antimony (V) chlorofluoride leaving the packed column is molten (O. Ruff Chem. Ber. 42, 4021 (1909); preferably, the temperature will be in excess of 80° C. and most preferably 90° to 100° C.

Under the preferred conditions of temperature and pressure, the antimony (V) chlorofluoride will be saturated with dissolved HCl as it leaves packed tower A. For that reason, the antimony (V) chlorofluoride will be passed down through the stripping column H into vessel B while a small but effective amount of nitrogen gas flows countercurrently to it via line 405. Nitrogen gas and stripped HCl exit the packed column H via line 406 to packed tower A from which it is exhausted via line 403. The pressure in vessel B and column H can be the same as or more or less than that of packed tower A. Preferably, the pressure in vessel B and column H is slightly higher than that in packed tower A so that gas from column H can be fed to tower A via line 406.

The antimony (V) chlorofluoride exiting vessel B via line 407 is substantially free of hydrogen halide. More particularly, the HCl content of the antimony (V) chlorofluoride exiting vessel B should be no more than 6% based on the weight of the antimony (V) chlorofluoride plus the HCl dissolved in it, preferably 1% or less dissolved HCl. The presence of HCl in the antimony (V) chlorofluoride presents several problems, all of which increase capital and operating costs for the process materially. An obvious problem created by the presence of HCl in the antimony compound is the need to remove it from the desired fluorinated products. In addition, HCl reacts with the antimony (V) chlorofluoride so as to liberate HF. That reaction gives several detrimental results. The most obvious one is that one must then subject the desired end-product to costly purification procedures, not the least of which is one occasioned by the need to break an azeotrope of HF with the desired end-product. Not only do such purification procedures increase operating costs materially, but they increase capital costs materially as well. Moreover, liberation of HF by reaction of HCl with the antimony (V) chlorofluoride decreases the HF efficiency for the process. The HF content of the desired fluorinated end-product should be no more than 1% by weight; more appropriately, it will be no more than 0.5% by weight, most preferably less than 0.01% by weight.

The antimony (V) chlorofluoride is fed from vessel B via line 407 to "T" 408, at which it is mixed with the haloalkane which is fed through line 409. The mixture of antimony chlorofluoride and haloalkane is fed to reactor C via line 410. The pressure in reactor C is usually lower than that in packed tower A and vessel B. If it is desired or necessary to operate reactor C at pressures higher than that in tower A, vessel B and column H, the antimony (V) chlorofluoride will be pumped from vessel B to reactor C. The process is most effective economically when reactor C is operated at a pressure between 100 psig and 200 psig, preferably 150 psig.

Reaction temperatures are substantially the same in each of packed tower A, vessel B, column H and reactor C. The reaction of antimony pentachloride with HF is mildly exothermic. Depending upon atmospheric temperature and reactor surface area per unit of volume, it may or may not be necessary to supply heat or cooling to packed tower A and/or vessel B and/or column H. On the other hand, it is necessary to supply energy to reactor C, because as fluorinated products are produced in it having lower and lower boiling points, those products come out of solution into the vapor phase, an endothermic process.

The reaction mixture which exits reactor C is made up of a mixture of one or more fluorinated products in the vapor state and spent antimony chlorofluoride in the liquid state, with some of the organic components of the reaction mixture dissolved in the latter. That mixture is fed via line 411 to vapor-liquid separator D which is operated at the same pressure as reactor C. The gaseous products and any unreacted haloalkane are removed from separator D via line 412, and the liquid is fed via line 413 to packed stripper tower E in which substantially all organic components dissolved in the spent antimony (V) chlorofluoride are removed by a stripping gas, such as HCl, $CHF_3$ or nitrogen, which is fed to the bottom of stripping tower E via line 414. The gaseous reaction products, stripping gas and any unreacted haloalkane are removed from stripping tower E via line 415. The stripped spent antimony (V) chlorofluoride is removed from the bottom of stripping tower E into a pump tank F in which it is accumulated and continuously recycled via line 416, pump G and line 401 to packed tower reactor A.

Stripper tower E, unlike vessels A, B, C, and H, is operated at low pressure, preferably at about one or two psig. One takes a pressure drop to that pressure in line 413 through control valve 417. The gaseous products removed via line 415 can be separated for recovery of desired fluorinated products and for recycle of underfluorinated components. The spent antimony (V) chlorofluoride which exits pump tank F via line 416 is fed to the suction side of pump G which must have the capability of producing enough pressure to go from its suction pressure of about one to two psig to the higher reaction pressure preferably used in packed tower reactor A.

In all embodiments of the invention, the temperature employed, the mol ratio of haloalkane to antimony (V) chlorofluoride, and the contact time between the antimony (V) chlorofluoride and the haloalkane used will depend upon the degree of fluorination of the antimony pentachloride and the identity of end product that is desired. Generally, a combination of a high level of haloalkane with a low degree of fluorination of antimony pentachloride will favor monofluorination whereas a combination of a low level of haloalkane with a high degree of fluorination in the antimony pentachloride will favor multiple fluorination. The fluorinated haloalkanes obtained will generally be a mixture of fluorinated compounds. A notable feature of the present invention is that in contrast to the prior art processes, the fluorinated haloalkanes are produced without the coproduction of equivalent amounts of hydrogen halide. If the antimony (V) chlorofluoride is thoroughly degassed of hydrogen halide before introduction into the haloalkane fluorination reactor, the fluorinated haloalkane produced will be substantially completely free of hydrogen halide. The amount of hydrogen halide present in the crude fluorinated haloalkane will be considerably less than that obtained in prior art processes in which a haloalkane is reacted with hydrogen fluoride in the presence of an antimony pentahalide. The present invention thus provides the advantages of producing crude fluorinated haloalkane substantially free of hydrogen fluoride which makes the recovery of fluorinated haloalkanes considerably easier and more economical by eliminating a number of distillation systems which would have required high pressures and costly refrigeration, and by eliminating costly systems for separating the azeotropes of HF and the fluorocarbons. At the same time it provides as a by-product commercially valuable hydrogen chloride gas of high purity.

The term "haloalkane" is meant to include those alkanes substituted with at least one halogen atom other than a fluorine atom; i.e., chlorine, bromine or iodine, and that are fluorinatable by the antimony (V) chlorofluorides under the conditions described herein. The haloalkane may also contain fluorine atoms; provided that at least one nonfluorine halogen atom is present. The preferred fluorinatable haloalkanes are those wherein the halogen substituent is chlorine since they are lower in cost and readily available and have less tendency to undergo side reactions in the fluorinator, such as rearrangement reactions. Theoretically, any fluorinatable haloalkane which can be readily introduced into the haloalkane fluorinator can be used in the present process, but haloalkanes containing one to three carbon atoms are usually employed. Preferred haloalkanes are those containing one to two carbon atoms while those containing one carbon atom are most preferred. The preferred haloalkanes of two carbon atoms are tetrachloroethanes, pentachloroethane and hexachloroethane. Those haloalkanes may be supplied directly to the haloalkane fluorination reactor, or they may be supplied by the introduction of a combination of dichloroethylenes, trichloroethylene or tetrachloroethylene with chlorine to the haloalkane fluorinator. Those combinations respectively form tetrachloroethanes, pentachloroethane and hexachloroethane in situ. The haloalkane reactants can also be fluoroalkanes such as 1,1,2-trichloro-1-fluoroethane which can be prepared by reacting HF with trichloroethylene (i.e., 1,1,2-trichloroethene). The preferred one carbon atom haloalkanes are chloroform and carbon tetrachloride.

As with the haloalkanes, it is theoretically possible to prepare any chlorofluoroalkane by use of the process of the present invention. However, usually the chlorofluoroalkane so produced contains one to three carbon atoms and preferably one to two carbon atoms. Exemplary of the fluoroalkanes to which the process of this invention can be directed are trichlorofluoromethane; dichlorodifluoromethane; dichloromonofluoromethane; monochlorodifluoromethane; trifluoromethane; 1,1,2,2-tetrachloro-1,2-difluoroethane; 1,1,2-trichloro-1,2,2-trifluoroethane; 1,2-dichloro-1,1,2,2-tetrafluoroethane; 2-chloro-1,1,1-trifluoroethane; 2,2-dichloro-1,1,1-trifluoroethane; and 2-chloro-1,1,1,2-tetrafluoroethane.

The following examples further illustrate the invention. Unless otherwise specified, all percentages are by weight and temperatures are in degrees Celsius.

EXAMPLE 1

This example demonstrates the continuous hydrofluorination of antimony pentachloride by continuously feeding antimony pentachloride to the top of a packed tower and reacting it with HF carried up the tower with gaseous HCl by-product of reaction. In this example the antimony (V) chlorofluoride is stripped with nitrogen to remove dissolved HCl before being continuously fed to a reactor to which chloroform is fed, thereby demonstrating the production of chlorofluorohydromethanes free of HF and HCl.

Figure 2:
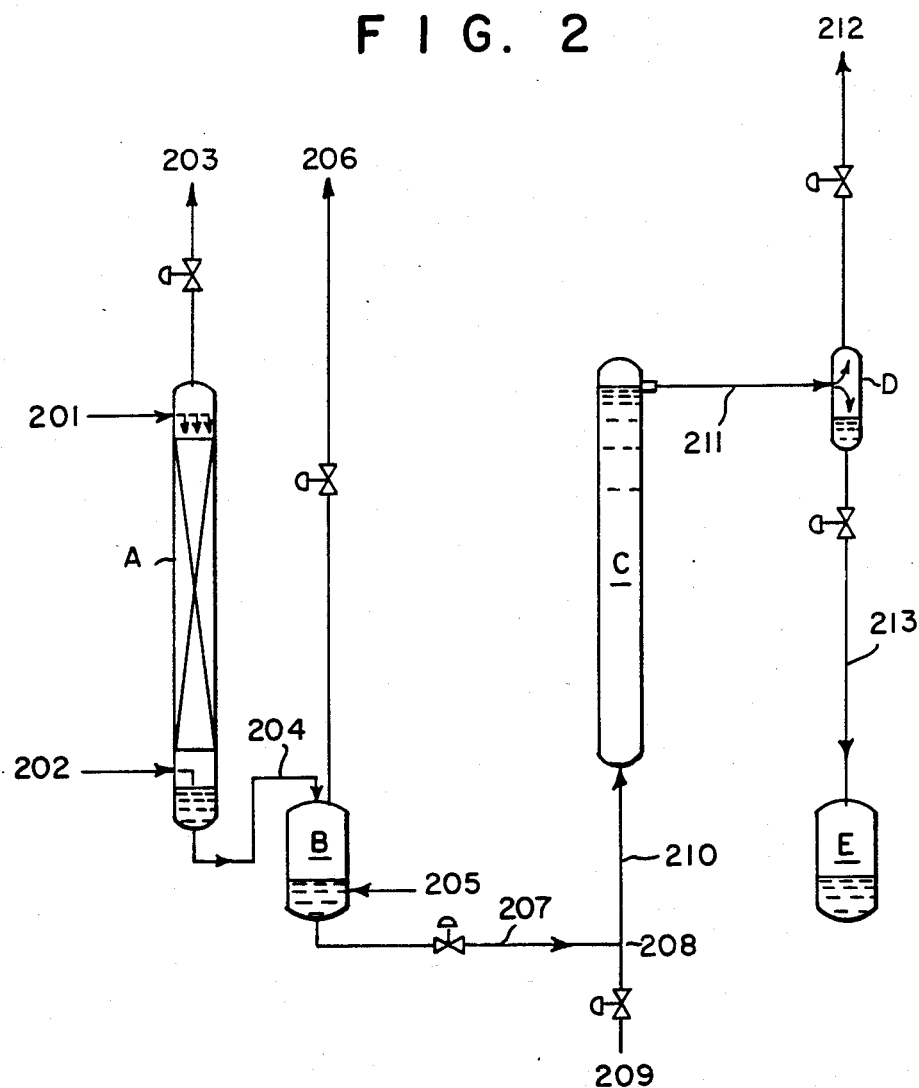
FIG. 2 depicts a modified embodiment of the invention in which by-product HCl is removed by purging, but in which there is no recycle of spent antimony (V) chlorofluoride after reaction with the haloalkane.

The experiments described in this example include a start-up period in which those running the experiment were becoming familiar with the equipment being used for the experiment. As a result, a variety of reaction conditions, viz., feed rates of reactants, temperatures and pressures, were used. Referring to FIG. 2, packed tower A used in this Example was a two-inch diameter Schedule 40, Alloy 20 pipe packed to a height of 27 inches with one quarter inch stainless steel Raschig rings, and reactor C was a 40-inch long, 3-inch diameter Schedule 40, Alloy 20 pipe which was steam jacketed to permit control of the reaction temperature. The liquid takeoff line 211 connected to reactor C was four and three-quarter inches below the top flange of the reactor. Reactor C contained seven equally spaced sieve plates (three-inch spacing) which served to stage the reactor, provide good mixing, and prevent bypassing. Each sieve plate was three inches in diameter and was fitted with a sealing ring on the outer periphery so as to prevent bypassing. Each sieve plate contained 5 one-quarter inch holes drilled in a symmetrical pattern.

Antimony pentachloride was fed continuously via line 201 at rates between 40 pounds and 61.6 pounds (0.142–0.206 lb-mol) per hour and distributed onto packing contained in tower A. Liquid HF was fed continuously at various rates between 2.4 and 4.4 pounds (0.120–0.220 lb-mol) per hour into the packing in the bottom of packed tower A using line 202. The system pressure was controlled between 260 and 275 psig and the temperature between 88° and 96° C. The HCl gas generated by the reaction of HF with antimony pentachloride passed up the tower A and was countercurrently contacted by the downflowing liquid stream of antimony pentachloride to remove unreacted HF contained in the vapor. Hydrogen chloride containing an average of 0.8 wt. % HF was vented continuously from tower A via line 203. The antimony (V) chlorofluoride produced in tower A was removed continuously via line 204 and accumulated in vessel B which was purged with nitrogen introduced through line 205 to remove dissolved HCl which was vented via line 206.

The antimony (V) chlorofluoride, typically containing 3.6 to 4.4 wt. % fluoride was fed continuously from vessel B via line 207 to a "T" 208 where it was mixed with chloroform fed continuously via line 209. The resulting reaction mixture was fed continuously via line 210 to reaction vessel C which was controlled at 192 to 197 psig and 90° to 110° C. The reaction mass, a mixture of vapor and liquid, was discharged from reaction vessel C via line 211 and fed continuously to a vapor-liquid separator D. The liquid phase containing the spent antimony (V) chlorofluoride was removed continuously from vessel D via line 213 and accumulated in vessel E. The vapor from vessel D was removed continuously via line 212, sampled and analyzed. Information as to charge rates and the like are given in Table I, and information as to crude product composition are given in Table II.

TABLE I

| | Run No. | |
|---|---|---|
| | 1 | 2 |
| Antimony (V) Chlorofluoride (4.42–4.31% Fluoride) Feed Rate, | | |
| Lbs/Hr | 45.5 | 45.8 |
| Lb-Mol Fluoride/Hr | 0.106 | 0.104 |
| Chloroform Feed Rate, | | |
| Lbs/Hr | 6.8 | 6.0 |
| Lb-Mol/Hr | 0.057 | 0.050 |
| Fluoride to Chloroform | | |
| Mol Ratio in Feed | 1.85 | 2.08 |

TABLE II

| Component | Composition in Mol % | |
|---|---|---|
| HF | Not Detected | Not Detected |
| Antimony Pentahalide | 2.3 | 3.3 |
| Chlorine | 3.0 | 2.0 |
| Chloroform | 30.2 | 6.9 |
| Dichlorofluoromethane | 6.9 | 6.5 |
| Chlorodifluoromethane | 51.5 | 64.3 |
| Trifluoromethane | 6.1 | 17.0 |

Run 1 is an experiment in which the fluoride in the antimony (V) chlorofluoride to chloroform mol ratio in the feed is deficient of that needed to convert all of the chloroform to chlorodifluoromethane; Run 2 is an experiment in which the fluoride in antimony (V) chlorofluoride to chloroform mol ratio in the feed is in excess of that needed to do so. In neither run was there any HF present in the crude product gases.

EXAMPLE 2

The equipment configuration of Example 1 shown in FIG. 2 was used to demonstrate the continuous hydrofluorination of antimony pentachloride with HF in packed tower A, followed by the continuous fluorination of chloroform in reactor C by continuously flowing the antimony (V) chlorofluoride from reactor A to reactor C.

Antimony pentachloride was fed continuously through line 201 at 49 lb. (0.163 lb-mol) per hour and distributed onto packing in tower A. Liquid HF was fed continuously at 3.4 lb. (0.169 lb-mol) per hour into the liquid hold-up in the bottom of tower A. The system pressure was controlled at 265 psig and the temperature at 85° C. The HCl generated by the reaction of HF with antimony pentachloride passed up the tower as a vapor and countercurrently contacted the downflowing liquid stream of antimony pentachloride to convert unreacted hydrogen fluoride. The HF content of the HCl stream, leaving tower A continuously via line 203 was 0.25 wt. %, giving 99.7% utilization of the HF fed to the reactor. The antimony (V) chlorofluoride produced in tower A, having a fluoride content of 6.63 wt. % (closely corresponding to SbCl$_4$F), was fed continuously via line 204 to vessel B.

The solubility of HCl in SbCl$_4$F at various pressures and temperatures had been determined in separate experiments. Using those data, the calculated HCl solubility in the antimony (V) chlorofluoride produced in this example would be 4.7 wt. %. Under those conditions, 63% of the HCl produced from the HF reaction in reactor A was removed directly from tower A via line 203, leaving 37% of that produced dissolved in the antimony (V) chlorofluoride. The antimony (V) chlorofluoride was not purged with nitrogen to remove dissolved HCl as in Example 1.

The antimony (V) chlorofluoride at about 85° C. was fed continuously from vessel B via line 207 to a "T" 208 where it was mixed with chloroform fed through line 209 at about 102° C. The reaction mixture was fed via steam-jacketed line 210 to reaction vessel C which was operated at about 190 psig and 107° C. The resulting reaction product was discharged continuously from reactor C via line 211 to a vapor/liquid separator D. The spent antimony (V) chlorofluoride (1.4 wt. % fluoride) was removed from separator D via line 213 and collected in receiver E. The gas stream that separated in vessel D was removed via line 212 and sampled for analysis. Feed rates for reactor C are given in Table III, and crude product composition is given in Table IV.

TABLE III

| Antimony (V) Chlorofluoride (6.63 wt. % fluoride) Feed Rate | |
|---|---|
| Lbs/Hr | 48.9 |
| Lb-Mol Fluoride/Hr | 0.170 |
| Chloroform Feed Rate | |
| Lbs/Hr | 13.1 |
| Lb-Mol/Hr | 0.120 |
| Fluoride to Chloroform | |
| Mol Ratio in Feed | 1.417 |

TABLE IV

| Component | Composition in Mol % |
|---|---|
| HF | 1.9 |
| Antimony (V) Chlorofluoride (1.4 Wt. % Fluoride) | 1.9 |
| HCl | 32.8 |
| Cl$_2$ | 0.4 |
| Chloroform | 10.1 |
| Dichlorofluoromethane | 21.8 |
| Chlorodifluoromethane | 30.4 |
| Trifluoromethane | 0.7 |

By calculation, this example demonstrates that even without stripping dissolved HCl from the antimony (V) chlorofluoride produced in reactor A, the amount of inorganic fluoride contained in the crude organic product vapor stream is only 1.6% of the fluoride fed to reactor C.

CONTROL 1

The results of Examples 1 and 2 representative of this invention are compared with those of the prior art technology such as that described in U.S. Pat. No. 2,005,705, wherein the hydrogen fluoride and chloroform are continuously and simultaneously fed into a reaction vessel containing a static charge of antimony pentachloride.

A commercial reactor was operated at 78° C. and 178 psig. The reactor off-gases were directly fractionated to return high boilers such as antimony pentachloride, chloroform and dichlorofluoromethane to the reaction vessel. The crude product coming from the fractionator was sampled and analyzed giving the results set forth in Table V.

TABLE V

| Component | Mol % |
|---|---|
| HF | 8.8 |
| Antimony Pentachloride | .02 |
| HCl | 61.3 |
| Chlorodifluoromethane | 28.5 |
| Trifluoromethane | 1.4 |

Based on the mols of HF and HCl leaving the system, 12.5% of the HF fed to the system reactor was leaving in the crude organic product. These results are compared below with those of Examples 1 and 2 in Table VI.

TABLE VI

| | Example 1 Process of This Invention With HCl Stripped From Antimony (V) Chlorofluoride | Example 2 Process of This Invention With 37% of HCl Fed to Organic Fluorinator | Control 1 Process of The Prior Art With 100% of HCl Made in Organic Fluorinator |
|---|---|---|---|
| % of HF Fed To System Contaminating Crude Organic Product as Free HF | Not Detected | 1.3 | 12.5 |
| Efficiency of Fluoride Utilization | 100% | 97.8% | 87.3% |
| HCl Content of Crude Gaseous Products (mol %) | Not Detected | 32.8% | 61.3% |

Table VI summarizes some of the advantages of this invention. It shows that when the most preferred embodiment (as exemplified by Example 1) is carried out, neither HCl nor HF was detected in the crude gaseous reaction product. It additionally shows that even where one uses antimony (V) chlorofluoride having some HCl to be dissolved in it (as exemplified in Example 2), the amount of HF in the crude gaseous reaction is about 10% of that which is found in the prior art crude product, and the HCl content of the crude gaseous reaction product is approximately one-half of that of the prior art crude reaction product.

EXAMPLE 3

The equipment configuration shown in FIG. 2 was used to demonstrate the continuous hydrofluorination of antimony pentachloride with HF in reactor A, followed by the continuous fluorination of carbon tetrachloride in reactor C by continuously flowing the antimony (V) chlorofluoride from reactor A to reactor C.

Spent antimony (V) chlorofluoride containing 0.4 wt. % F was fed continuously through line 201 at 40 lb/hr and distributed onto packing in tower A. Liquid HF was fed at 3.2 lb/hr into the liquid hold-up in the bottom of tower A via line 202. The system pressure was controlled at 248 psig and the temperature at between 69° and 75° C. The HCl generated by the reaction of HF with antimony (V) chlorofluoride passed up the tower as a vapor and countercurrently contacted the downflowing liquid stream of antimony (V) chlorofluoride to convert unreacted hydrogen fluoride. The HCl left the tower A via line 203. The HF content of that HCl stream was 0.4 wt. % giving 99.2% utilization of the HF fed to the reactor. The antimony (V) chlorofluoride (fluoride content 8.14 wt. %) produced in tower A was fed continuously via line 204 to vessel B, but it was not purged with nitrogen to remove dissolved HCl as in Example 1.

The solubility of HCl in antimony (V) chlorofluoride had been experimentally determined in separate experiments. Using those data, the calculated HCl content of the antimony (V) chlorofluoride through solubility is 6.9 wt. %. Under these conditions, 57% of the HCl produced from the HF reaction in reactor A was removed directly via line 203, leaving 43% dissolved in the antimony (V) chlorofluoride.

The antimony (V) chlorofluoride at 69° C. was fed continuously at 37.5 lb/hr from vessel B via line 207 to a "T" 208 where it was mixed with carbon tetrachloride fed at 15.2 lb/hr through line 209 at 94° C. The reaction mixture was fed continuously via steam-jacketed line 210 to reactor vessel C which was operated at 92 psig and 100° to 103° C. Reactor C was discharged via line 211 to a vapor/liquid separator D. The spent antimony (V) chlorofluoride was removed from vessel D via line 213 to receiver E. The gas stream that separated in vessel D was removed via line 212 and was analyzed giving the results set forth in Table VII.

TABLE VII

| Component | Composition in Mol % |
|---|---|
| HF | 2.0 |
| Antimony (V) Chlorofluoride (.85 wt. % F) | 1.2 |
| HCl | 40.7 |
| Carbon Tetrachloride | 0.8 |
| Trichlorofluoromethane | 29.2 |
| Dichlorodifluoromethane | 25.6 |
| Chlorotrifluoromethane | 0.5 |

In this example of the total weight of fluorine leaving the reactor, 2.4% was as HF.

CONTROL 2

The results of Example 3 representative of this invention are compared with those of technology presently used in industry, such as that described in U.S. Pat. No. 2,005,705, wherein the hydrogen fluoride and carbon tetrachloride are continuously and simultaneously fed into a single reaction vessel containing a static charge of antimony pentachloride.

A commercial reactor was operated at 91° C. and 250 psig. The reactor off-gases were directly fractionated to return high boilers such as antimony pentachloride and carbon tetrachloride to the reaction vessel. The overhead crude product from the fractionator was sampled and analyzed giving the results set forth in Table VIII.

TABLE VIII

| Component | Mol % |
|---|---|
| HF | 8.7 |
| HCl | 60.1 |
| Trichlorofluoromethane | 2.3 |
| Dichlorodifluoromethane | 28.9 |

For this control, of the total fluorine leaving the reactor system, 12.7% was as unreacted HF. This compares to 2.4% for Example 3 in which the process of this invention was used to fluorinate carbon tetrachloride.

EXAMPLE 4

Figure 3:
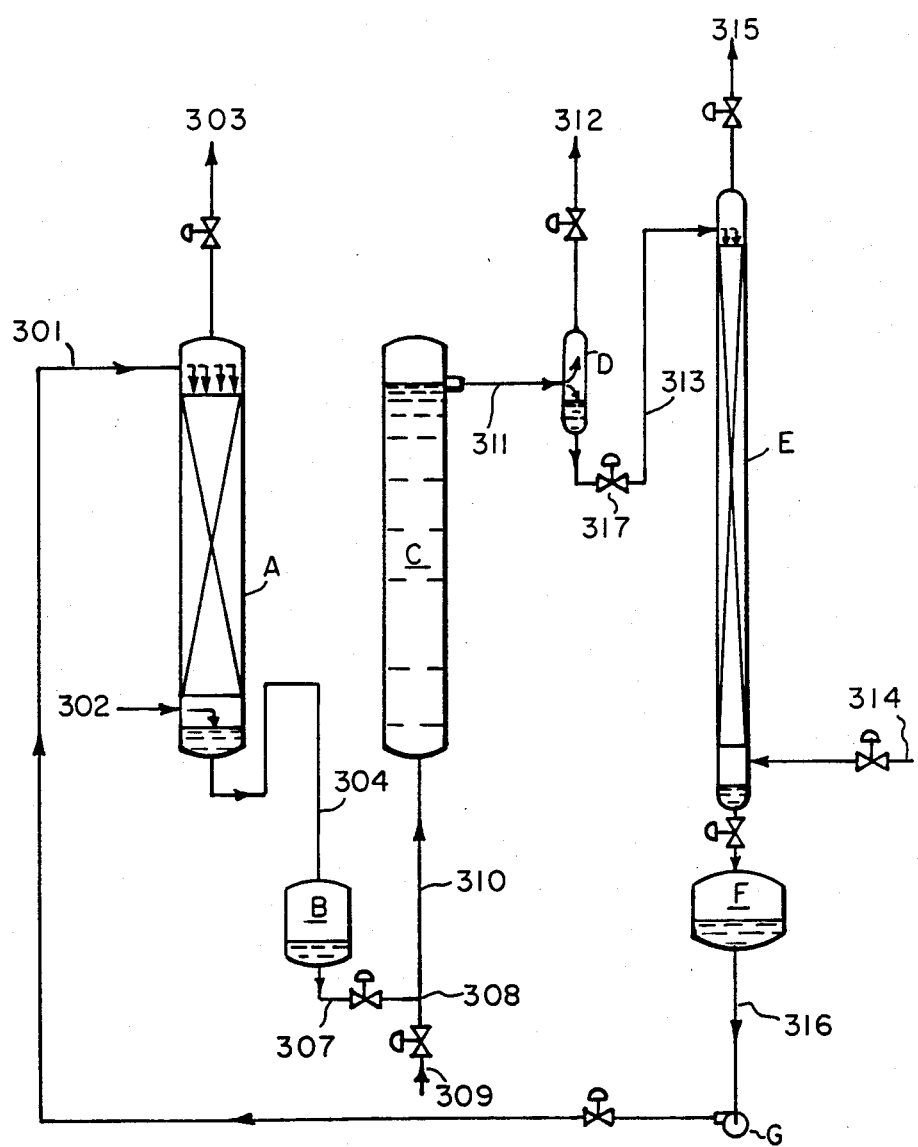
FIG. 3 shows a modification of the embodiment shown in FIG. 2 in which spent antimony (V) chlorofluoride is stripped of organic materials and recycled.

The equipment configuration shown in FIG. 3 was used to demonstrate the continuous fluorination of recycled spent antimony (V) chlorofluoride with HF in reactor A, followed by the continuous fluorination of chloroform in reactor C by continuously flowing the refluorinated antimony(V) chlorofluoride from reactor A and mixing it with the chloroform feed, separating the spent antimony (V) chlorofluoride liquid from the organic vapors generated in reactor C, and finally stripping the residual organics from solution in the spent antimony (V) chlorofluoride in stripper column E before it was recycled to reactor A to increase the fluorine content of the antimony (V) chlorofluoride fluorinating agent. The equipment descriptions for reactor A and reactor C are given in Example 1. Stripping column E was a 2-inch diameter Schedule 40, 316 stainless steel pipe packed to a height of 10 feet with one-quarter inch stainless steel Raschig rings.

Spent antimony (V) chlorofluoride containing 1.4 wt. % fluoride was recycled continuously using pump G and fed continuously to reactor A at about 134 lb/hr via line 301. The antimony (V) chlorofluoride feed contained 0.2 mol % residual chloroform after having been stripped in stripper column E. Reactor A was operated at 244 psig, the pressure being controlled by venting via line 303 by-product HCl which contained 0.35 mol % of organics. The antimony (V) chlorofluoride prepared in reactor A contained 8.05 wt. fluoride and was discharged continuously from the reactor at 72° C. and was fed continuously via line 304 to vessel B. Using a level control device in vessel B, the antimony (V) chlorofluoride was fed continuously via line 307 at 126.8 lb/hr and mixed at "T" 308 with chloroform fed continuously through line 309 at 32.3 lb/hr at a temperature of 110° C. This mixture of reactants was fed via line 310 to reactor C which was operated at about 174 psig and about 125° C. A liquid and vapor mixture was discharged from reactor C via line 311 to vapor/liquid separator D. The separated vapor stream was removed continuously via line 312, sampled and analyzed giving the results set forth in Table IX.

TABLE IX

| Component | Mol % |
| --- | --- |
| HF | 2.8 |
| HCl | 46.2 |
| Chlorine | 5.3 |
| Sb(V) Chlorofluoride | 0.5 |
| Chloroform | 2.1 |
| Dichlorofluoromethane | 5.5 |
| Chlorodifluoromethane | 35.0 |
| Trifluoromethane | 2.7 |

The spent antimony (V) chlorofluoride containing 10.1 mol % chloroform, 1.2 mol % dichlorofluoromethane, 7.5 mol % chlorodifluoromethane, and 0.4 mol % trifluoromethane was discharged continuously from the bottom of liquid/vapor separator D, its rate of discharge being controlled automatically by a level control device located in separator D. The pressure of the spent antimony (V) chlorofluoride at 125° C. was reduced from 174 psig to 4.5 psig in line 313, and the resulting mixture of liquid and vapor at 99° C. was fed continuously to the top of stripper tower E. Nitrogen was fed continuously to column E via line 314 at a rate of two lb/hr to countercurrently strip dissolved organics from the downflowing antimony (V) chlorofluoride. The stripped spent antimony (V) chlorofluoride was removed from the bottom of stripper column E and fed to pump tank F. Analysis of this material showed the only organic present to be chloroform at 0.2 mol % concentration. The stripped antimony (V) chlorofluoride was recycled continuously via line 316, pump G and line 301 to reactor A at about 134 lb/hr. The vapors from stripper column E were vented via line 315. Of the organics fed to stripper tower E, 99.1% of the organics were removed via line The composition of stream 315 was calculated by material balance to be that set forth in Table X.

TABLE X

| Component | Mol % |
| --- | --- |
| HCl | 18.3 |
| Sb(V) Chlorofluoride | 2.4 |
| Chloroform | 25.3 |
| Dichlorofluoromethane | 3.1 |
| Chlorodifluoromethane | 19.1 |
| Trifluoromethane | 0.90 |
| Nitrogen | 30.9 |

Based on the fluorine atoms leaving the system crude product vapors from reactor C and stripping tower E, utilization of HF to produce fluorinated organic products was 97.1% efficient. If desired, utilization efficiency can be increased even more by further lowering the amount of dissolved HCl in the antimony (V) chlorofluoride produced in reactor A before feeding it to reactor C, as demonstrated in Example 1.

I claim:

1. A continuous process for fluorinating haloalkanes comprising:
   continuously fluorinating antimony pentachloride to an antimony (V) chlorofluoride by continuously supplying hydrogen fluoride and antimony (V) pentachloride containing no more than 10% trivalent antimony to a first reaction zone while continuously removing by-product hydrogen chloride gas from the antimony (V) chlorofluoride thus produced,
   continuously feeding said antimony chlorofluoride to a separate reaction zone while continuously supplying a fluorinatable haloalkane containing at least one nonfluorine halogen atom to said separate reaction zone and reacting said antimony chlorofluoride with said haloalkane thereby replacing a portion of said nonfluorine halogen in said haloalkane with fluorine of said antimony chlorofluoride and recovering the fluorinated haloalkane or haloalkanes produced.

2. The process of claim 1 which said haloalkane is chloroform.

3. The process of claim 1 wherein said haloalkane is carbon tetrachloride.

4. The process of claim 1 in which spent antimony (V) chlorofluoride from the reaction with said haloalkane is recycled to said first reaction zone.

5. The process of claim 4 in which the haloalkane is chloroform.

6. The process of claim 4 in which the haloalkane is carbon tetrachloride.

7. The process of claim 1 wherein said antimony chlorofluoride contains no more than about 6 percent by weight of HCl.

8. The process of claim 4 in which at least a portion of said recycled spent antimony (V) chlorofluoride is contacted with a countercurrent flow of by-product hydrogen chloride.

9. The process of claim 8 in which the haloalkane is chloroform.

10. The process of claim 8 in which the haloalkane is carbon tetrachloride.

11. The process of claim 4 in which a portion of spent antimony (V) chlorofluoride from the reaction with said haloalkane is recycled to the reaction zone where hydrogen fluoride is supplied and the remaining portion is contacted with a countercurrent flow of by-product hydrogen chloride.

12. The process of claim 11 wherein said haloalkane is carbon tetrachloride.

13. The process of claim 11 in which said haloalkane is chloroform.

14. The process of claim 1 wherein HCl is removed from said antimony (V) chlorofluoride prior to its being reacted with said haloalkane by stripping said antimony compound with a small but effective amount of an inert gas.

15. The process of claim 14 wherein said haloalkane is chloroform.

16. The process of claim 14 wherein said haloalkane is carbon tetrachloride.

17. The process of claim 14 wherein HCl is removed from said antimony (V) chlorofluoride by contacting said antimony chlorofluoride countercurrently with nitrogen gas.

18. The process of claim 17 wherein said haloalkane is chloroform.

19. The process of claim 17 wherein said haloalkane is carbon tetrachloride.

20. The process of claim 1 wherein said fluorinated reaction products contain no more than 1 percent by weight of HF.

21. The process of claim 20 in which said haloalkane is chloroform.

22. The process of claim 20 in which said haloalkane is carbon tetrachloride.

23. The process of claim 4 wherein organic matter is removed from said spent antimony (V) chlorofluoride before recycle to the first reactor, whereby the HCl produced from the first reactor is substantially free of organic matter.

24. The process of claim 23 wherein said haloalkane is chloroform.

25. The process of claim 24 wherein said fluorinated reaction product comprises chlorodifluoromethane which is substantially free of an HF azeotrope therewith.

26. The process of claim 23 wherein said haloalkane is carbon tetrachloride.

27. The process of claim 2 wherein said recovered antimony (V) chlorofluoride contains between about 3 and 14% by weight fluorine.

28. The process of claim 3 wherein said recovered antimony (V) chlorofluoride contains between about 3 and 14% by weight of fluorine.

* * * * *